United States Patent [19]

Hedrich et al.

[11] Patent Number: 5,510,556
[45] Date of Patent: Apr. 23, 1996

[54] SATURATE REDUCTION IN NORMAL ALPHA OLEFINS USING A COBALT-CONTAINING TRANSALKYLATION CATALYST

[75] Inventors: Loren W. Hedrich, Kingwood; Alfred N. Kresge, Humble; Roger C. Williamson, Kingwood, all of Tex.

[73] Assignee: Chevron Chemical Company, San Ramon, Calif.

[21] Appl. No.: 299,989

[22] Filed: Sep. 1, 1994

Related U.S. Application Data

[63] Continuation-in-part of Ser. No. 881,905, May 12, 1992, Pat. No. 5,345,022, which is a continuation-in-part of Ser. No. 870,536, Apr. 17, 1992, abandoned.

[51] Int. Cl.$^6$ ..................................................... C07C 2/26
[52] U.S. Cl. ............................................................. 585/522
[58] Field of Search .............................................. 585/522

[56] References Cited

U.S. PATENT DOCUMENTS

| | | |
|---|---|---|
| 2,781,410 | 2/1957 | Ziegler et al. ................. 260/683.15 |
| 2,978,523 | 4/1961 | Coyne et al. .................. 260/683.15 |
| 3,035,104 | 5/1962 | Harvey et al. ................. 260/683.15 |
| 3,277,203 | 10/1966 | Keehan et al. ..................... 260/677 |
| 3,363,021 | 1/1968 | Tucci ................................. 260/677 |
| 3,482,000 | 12/1969 | Fernald et al. ................ 260/683.15 |
| 3,510,539 | 5/1970 | Fernald et al. ................ 260/683.15 |
| 3,702,345 | 11/1972 | Fernald et al. ................ 260/683.15 |
| 4,918,254 | 4/1990 | Diefenbach et al. ................ 585/328 |

*Primary Examiner*—Asok Pal
*Assistant Examiner*—Bekir L. Yildirim
*Attorney, Agent, or Firm*—Charles D. Holland

[57] ABSTRACT

Disclosed is a process for producing normal alpha olefins having less than 1.0% saturates content, and typically no more than 0.40% saturates content. The process involves forming a mixture of normal alpha olefins and tri(higher) alkyl aluminum compounds, contacting this mixture with a cobalt-containing transalkylation catalyst, and hydrolyzing the normal alpha olefin/transalkylation catalyst mixture to minimize the amount of saturates formed. In one embodiment, the catalyst is a cobalt- and nickel-containing transalkylation catalyst. After hydrolysis, the resulting normal alpha olefins contain essentially no Group VIII metal that is capable of transalkylation.

20 Claims, No Drawings

SATURATE REDUCTION IN NORMAL ALPHA OLEFINS USING A COBALT-CONTAINING TRANSALKYLATION CATALYST

This application is a continuation-in-part application of U.S. Ser. No. 07/881,905, filed May 12, 1992, now U.S. Pat. No. 5,349,022, which is a continuation-in-part of U.S. Ser. No. 07/870,536, filed Apr. 17, 1992, now abandoned.

BACKGROUND OF THE INVENTION

Normal alpha olefins (NAO) are produced commercially using ethylene and trialkyl aluminum compounds. The preferred trialkyl aluminum compound is triethyl aluminum (TEA). In this oligomerization or "growth" reaction, a hydrocarbon group, for example, an alkyl group on an aluminum atom containing n ethylene units, can add an ethylene molecule to become an alkyl group of n+1 ethylene units. Different alkyl groups on the aluminum atom can contain different numbers of ethylene units. In order to distinguish them from the original trialkyl aluminum catalysts, the products of this oligomerization reaction will be referred to herein as "tri(higher)alkyl aluminum compounds."

The tri(higher)alkyl aluminum compounds are subjected to a transalkylation (sometimes called a "displacement") reaction which occurs concurrently with the oligomerization reaction, thereby forming alpha olefins. This transalkylation consists of two steps. These are, first, thermal decomposition of the tri(higher)alkyl aluminum compounds into an aluminum hydride and alpha olefin(s), followed by rapid reaction of the hydride with the excess ethylene in the reaction mixture to regenerate an ethyl group on the aluminum which can start another oligomerization cycle.

The resulting mixture comprises alpha olefins, triethylaluminum, and some amount of residual tri(higher)alkyl aluminum compound(s) which have not undergone the transalkylation reaction. This mixture is subjected to caustic treatment (hydrolysis) to decompose the triethylaluminum compounds. Unfortunately, this hydrolysis also decomposes the residual tri(higher)alkyl aluminum compounds, which typically results in a product containing about 1 to 1.5 weight percent, based on the weight of the product, of undesired saturated alkanes ("saturates" or "paraffins") in the product, rather than a product which contains only the desired alpha olefins. Because these saturates have boiling points close to the desired alpha olefins, they are very difficult to remove from the product by, e.g., distillation.

The resulting mixture is separated into an aqueous and an organic phase, and, after settling, the organic phase is water-scrubbed (to remove residual caustic and aluminum compounds) and distilled to give the various even-numbered alpha olefin cuts from $C_4$ up through $C_{30}$ and higher. The normal alpha olefins produced, particularly the $C_{12}$, $C_{14}$, and $C_{16}$ alpha olefins, have utility for the production of detergents. The $C_4$, $C_6$ and $C_8$ olefins are useful for preparing linear low density polyethylene. The $C_{10}$ olefin can be converted to oligomers useful as synthetic lubricants. As noted above, the olefin cuts will typically contain approximately about 1 to 1.5 weight percent paraffin, the paraffin being formed in the caustic hydrolysis step. In recent years, products containing lower paraffin contents have become available using other technologies. This has put pressure on the industry to upgrade its product.

Processes for making normal alpha olefins are disclosed in several U.S. patents. U.S. Pat. No. 2,781,410, issued Feb. 12, 1957 to Ziegler et at., discloses a process for the polymerization of ethylene to butene, hexene and higher olefins by contacting ethylene and a trialkyl aluminum compound. This causes the aforementioned "growth" reaction. It is disclosed that the range of temperature of "genuine catalysis" can be extended in the downward direction if "to the main catalysts aluminum trialkyl, nickel, cobalt or platinum is added as an activator."

U.S. Pat. No. 2,978,523, issued Apr. 4, 1961 to Coyne et at., discloses that prior processes for making higher olefins from lower olefins had involved the reaction of a trialkyl aluminum compound and ethylene to form the oligomerization product. After forming the product, it was heated in the presence of an additional quantity of ethylene and a finely divided metal catalyst, such as finely divided nickel. Coyne et at. disclose that these metal catalysts can include nickel, cobalt, palladium, and certain iron compounds. Their preferred catalyst is nickel or a nickel compound which will react with the trialkyl aluminum. Finely divided nickel metal, Raney nickel, nickel acetylacetonate, and nickel naphthanate are specifically disclosed. It is disclosed that the amount of catalyst used can vary greatly, and when the preferred catalyst is employed, the amount used may vary from about 0.001 to 0.1 percent based on the weight of the oligomerization product present.

U.S. Pat. No. 3,035,104, issued May 15, 1962 to Harvey et at., discloses that a trialkyl aluminum oligomerization product can be reacted with ethylene in the presence of about 0.01–1.0 tool percent of finely divided iron, preferably about 0.1 to 0.5 mol percent and about 0.001 to 0.01 mol percent, preferably about 0.001 mol percent of finely divided nickel for a time sufficient to displace the alkyl groups combined with the aluminum. The amounts of catalyst are based on the oligomerization product feed.

U.S. Pat. No. 3,277,203, issued Oct. 4, 1966 to Keehan et al., discloses the displacement of olefins from aluminum oligomerization product at elevated temperatures. In one displacement method, ethylene is reacted with aluminum alkyl oligomerization product in the presence of a finely divided metal catalyst, such as finely divided nickel. It is further disclosed that, while the catalyzed displacement reaction is very effective in providing the desired olefins, the use of a catalyst has disadvantages in that the catalyst is difficultly removable from the aluminum alkyl and may prevent the reuse of the latter material in the oligomerization process. Also, in the separation of olefins formed in the displacement reaction from the aluminum alkyl, for example, by distillation, the presence of the catalyst often produces undesirable reactions, such as reverse displacement and isomerization of olefins.

U.S. Pat. No. 3,363,021, issued Jan. 9, 1968 to Tucci, discloses a process for removing an aluminum trialkyl from a mixture which contains hydrocarbons and said aluminum trialkyls by subjecting the mixture to hydrolysis with water to convert the aluminum alkyls to the corresponding aluminum hydroxides, and the treated mixture can then be subjected to distillation to recover the hydrocarbons. As an alternative to this process, Tucci discloses a process which comprises treating the mixture with an ether, an amine or a sulfine to form a complex between the aluminum trialkyl and the ether, amine or sulfine, treating the complex with sodium, potassium, rubidium or cesium fluoride, cesium chloride or a complex of an aluminum trialkyl and one of such alkali metal halides, thereby freeing the ether, amine or sulfine from the first-named complex and forming a resulting complex between the first-named aluminum trialkyl and one of the defined alkali metal halides.

U.S. Pat. No. 3,482,000, issued Dec. 2, 1969 to Fernald et al., discloses a process for the polymerization of ethylene to normal and branched alpha olefins in the presence of an organometallic catalyst, such as triethyl aluminum. Fernald et al. state that a high selectivity toward normal alpha olefins is achieved by performing the reaction in a tubular reaction zone wherein the amount of polymer increases throughout the length of the reactor tube. The reaction temperature is between about 180° C. and 240° C., there is from about $1\times10^{-4}$ to about $1\times10^{-2}$ mols of catalyst per mol of ethylene, and the polymerization proceeds until there is a conversion of at least about 30 percent of said ethylene to polymer product.

U.S. Pat. No. 3,510,539, issued May 5, 1970 to Fernald et al., discloses a process for the production of alpha olefins from ethylene in the presence of trialkyl aluminum catalyst and solvent in a tubular reactor immersed in a bath of heat exchange fluid wherein no catalyst and solvent are added to the ethylene until the ethylene is preheated to full reaction temperature in an upstream portion of the tubular reactor, and the reaction then occurs at a constant temperature in a downstream portion of the tubular reactor.

U.S. Pat. No. 3,702,345, issued Nov. 7, 1972 to Fernald et al., discloses a process wherein ethylene is treated with an aluminum hydrocarbon to obtain a product predominating in normal alpha olefins. The process involves heating said product at an increased temperature level for a short period of time prior to recovery of the normal alpha olefins.

U.S. Pat. No. 4,918,254, issued Apr. 17, 1990 to Diefenbach et al., discloses a nickel-catalyzed displacement reaction in which the alkyl groups in trialkyl aluminum are displaced by alpha olefins in the presence of a nickel catalyst. The displacement is said to be fast and the catalyst is then poisoned with a catalyst poison such as lead to prevent undesired reactions such as isomerization of alpha olefins to internal olefins or dimerization to vinylidene olefins. The amount of nickel required to catalyze the reaction is said to be very low, on the order of parts per million (ppm). A useful range is said to be about 1–100 parts by weight nickel per million parts of reaction mixture. A preferred range is said to be 2–20 ppm, and a more preferred concentration is said to be 2–10 ppm.

A process has now been discovered which produces normal alpha olefins having lower paraffin content while at the same time resulting in minimal or substantially no isomerization of the alpha olefins.

SUMMARY OF THE INVENTION

In one embodiment, the present invention provides a new process for producing normal alpha olefins having low saturates content. This process comprises:

(a) contacting a trialkyl aluminum compound and ethylene under alpha-olefin formation conditions thereby producing a mixture comprising normal alpha olefins and tri(higher)alkyl aluminum compounds;

(b) contacting at least a portion of said mixture and sufficient ethylene, in the presence of a Group VIII metal-containing transalkylation catalyst, thereby transalkylating substantially all of said tri(higher)alkyl aluminum compounds, said transalkylation catalyst being used in an amount and under conditions which cause transalkylation of said tri(higher)alkyl aluminum compounds, but not isomerization of said normal alpha olefins; and (c) contacting the product of step (b) with a sufficient amount of aqueous acid or caustic, and water, to produce an organic phase and an aqueous phase, wherein said organic phase is substantially metal-free.

Preferably an alpha olefin fraction containing $C_{12}$ compounds having a dodecane content of less than about 0.3 wt % and a 2-dodecene content of less than about 0.3 wt %, both relative to the 1-dodecene content, is produced.

The present invention also provides an improved process for producing alpha olefins by contacting a trialkyl aluminum compound and ethylene under alpha olefin formation conditions, thereby producing a mixture comprising normal alpha olefins and tri(higher)alkyl aluminum compounds, and hydrolyzing said mixture of normal alpha olefins and tri(higher)alkyl aluminum compounds, wherein the improvement comprises contacting said mixture of normal alpha olefins and tri(higher)alkyl aluminum compounds, prior to hydrolysis, with ethylene and a Group VIII metal-containing transalkylation catalyst under transalkylation conditions, said transalkylation catalyst being used in an amount and under conditions sufficient to cause transalkylation but insufficient to cause isomerization of said normal alpha olefins.

In another embodiment, the present invention provides a method of removing catalyst from a hydrocarbon stream comprising trialkyl aluminum compounds, tri(higher)alkyl aluminum compounds and a Group VIII metal-containing transalkylation catalyst, said method comprising:

(a) reacting a hydrocarbon stream comprising normal alpha olefins, trialkyl aluminum compounds, tri(higher)alkyl aluminum compounds and a Group VIII metal-containing transalkylation catalyst with acid or caustic for a sufficient time to convert substantially all of said aluminum compounds and transalkylation catalyst to caustic- or water-soluble compounds;

(b) separating the resulting mixture into an aqueous phase and an organic phase; and (c) contacting said organic phase with water in a sufficient amount and for a sufficient amount of time to produce a normal alpha olefin stream which is substantially free of aluminum compounds and Group VIII metal.

Among other factors, the present invention is based on the discovery that, when a very small amount of a Group VIII metal-containing transalkylation catalyst is used to transalkylate the tri(higher)alkyl aluminum compound(s) present in a normal alpha olefin reaction mixture, saturates content in the normal alpha olefin product is minimized, while at the same time minimizing isomerization of the alpha olefins to internal olefins.

DETAILED DESCRIPTION OF THE INVENTION

A new method has now been discovered for producing normal alpha olefins containing low amounts of paraffins or saturates, while at the same time minimizing isomerization of the alpha olefins. The method of the present invention involves an alpha olefin formation reaction in which trialkyl aluminum compounds are reacted with ethylene, a saturates-minimization step, and a metals-recovery step.

Alpha Olefin Formation Reaction

A trialkyl aluminum compound is reacted with ethylene under alpha olefin formation conditions, such as 370° F. to 430° F. and 2500 to 5000 psi, to produce a mixture comprising alpha olefins and tri(higher)alkyl aluminum compounds. Typically, the alpha olefins contain from 4 to 30 or more carbon atoms. The trialkyl aluminum catalyst employed herein can be defined by the following structural formula:

 (I)

wherein $R^1$, $R^2$, and $R^3$ can be any hydrocarbon substituent having m carbon atoms. An effective catalyst is a trialkyl aluminum where the alkyl groups have from 2 to 30 or more carbon atoms, preferably from 2 to 20 carbon atoms. Examples of such catalysts which can be employed are $Al(CH_3)_3$, $Al(C_2H_5)_3$, $Al(C_3H_7)_3$, $Al(n—C_4H_9)_3$, $Al(i—C_4H_9)_3$, $Al(C_5H_{11})_3$, $Al(C_9H_{11})_3$, $Al(C_{12}H_{25})_3$, $Al(C_{16}H_{33})_3$, etc. As discussed above, the alkyl groups are generally not the same after oligomerization begins. Also, since it is generally desirable to produce alpha olefins which contain an even number of carbon atoms, the trialkyl aluminum catalysts which contain even numbered alkyl groups are preferred. While the catalysts containing odd-numbered alkyl groups can be used, they will produce mixtures of odd- and even-numbered olefins, which may be difficult to separate from each other.

As used herein, the term "trialkyl aluminum compounds" refers to the catalysts described in the preceding paragraph, e.g., triethyl aluminum. The term "tri(higher)alkyl aluminum compounds" refers to trialkyl aluminum compounds which have had at least one ethylene unit added to it. These tri(higher)alkyl aluminum compounds can be described by the following formula:

 (II)

where $R^4$, $R^5$, $R^6$ are each independently either the same as $R^1$, $R^2$, or $R^3$ in formula (I), or a hydrocarbon substituent, e.g. alkyl, having m+2x carbon atoms where x is the number of ethylene units added to any of $R^1$, $R^2$ or $R^3$ to form $R^4$, $R^5$ and/or $R^6$, with the proviso that at least one of $R^4$, $R^5$, and $R^6$ has at least one added ethylene unit.

The amount of trialkyl aluminum catalyst used is not critical. It can be present in an amount from about $1 \times 10^{-4}$ to about $1 \times 10^{-2}$ moles, preferably from about $1.5 \times 10^{-4}$ to about $5.0 \times 10^{-3}$ moles, per mole of ethylene.

The catalyst can be used as such, but preferably is dispersed in an inert hydrocarbon diluent. Since it is desired to produce a liquid alpha olefin product, rather than a relatively high molecular weight solid polymer, the trialkyl aluminum catalyst should be substantially free of catalyst components, such as, for example, $TiCl_4$, which will produce relatively high molecular weight solid polymers.

Hydrocarbon diluents, such as high molecular weight olefinic materials, naphthenes, or alkyl aromatics are preferred diluents. A recycle stream comprising the higher alpha olefins is a preferred diluent. An advantageous diluent that can be used comprises a $C_{18}$ or $C_{20}$ or higher alpha olefin recycle stream, for example, $C_{22}$ to $C_{28}$ alpha olefin recycle stream.

The diluent is especially beneficial in the initial stages of the reaction, i.e., near the zone of the reactor tube where ethylene and the trialkyl aluminum catalyst are first contacted with each other. After the reaction proceeds to a significant extent, the product itself functions as diluent and eventually far exceeds in quantity the initially-added diluent.

The trialkyl aluminum catalyst, which is continuously added to the reactor, is advantageously diluted in diluent to any suitable concentration range, such as between about 0.5 to about 50% by weight, preferably between about 2 and about 15% by weight. The concentration of catalyst in the diluent will depend upon both the quantity of diluent desired in the system and upon the desired ratio of catalyst to ethylene charge.

Upon addition of catalyst and diluent to the ethylene charge in the reactor, substantially all the catalyst remains in the diluent. In order to encourage production of normal alpha olefins in the reactor, it is important to rapidly dissolve the ethylene in the liquid diluent phase containing catalyst. Under the temperature and pressure conditions of the reactor a substantial quantity of ethylene is readily dissolved in the liquid diluent, enabling the reaction to proceed rapidly. The upper pressure range is not critical and can be as high as about 1000 atmospheres, or even higher. The lower pressure range is critical and should be sufficiently high so that most of the alpha olefin product is a liquid under reaction conditions and so that most of the catalyst and most of the ethylene are dissolved or dispersed in the liquid. After there has been a conversion of about 30 to about 90 mole percent, preferably about 50 to about 75 mole percent, of ethylene, which will involve a residence time of at least about 5 minutes, preferably about 20 to about 120 minutes, there is sufficient liquid product to dissolve substantially all the ethylene and produce a single homogeneous phase in the reactor. Thus, the pressure in the reactor should at all times be at least about 1000, and preferably at least about 2000 psig.

The reaction temperature can range from about 285° F. to about 615° F., preferably from about 350° F. to about 430° F., more preferably from about 380° F. to about 420° F. Low temperatures favor the oligomerization reaction and will result in a higher average molecular weight product. At high temperatures, the average molecular weight will be lower because transalkylation reactions predominate. The proportion of $C_{12}$ alpha olefin in the product tends to remain relatively constant with temperature changes within the most preferred range of this invention. However, lower temperatures favor a relatively higher proportion of product above $C_{12}$, and higher temperatures favor a relatively higher proportion of product below $C_{12}$.

It is important to maintain conversion levels of ethylene below about 75 mole percent, because at higher conversions production of branched olefins (e.g., vinylidenes) increases sharply. The reason is that at high conversion levels the proportion of product olefin to ethylene in the reactor becomes sufficiently high for the product olefin to compete significantly with the ethylene in the oligomerization reaction. The participation in the oligomerization reaction of any olefin higher than ethylene results in a vinylidene product.

The reactor is desirably an elongated tubular reactor. A preferred ratio of length to internal width is from about 200:1 to about 100,000:1, more preferably within a range of about 2000:1 to about 50,000:1.

When it is desired to terminate the reaction, the product is withdrawn from the tubular reactor. The temperature and pressure are reduced, whereupon most of the gaseous olefins are flashed off. The product is optionally filtered to remove solid polymers.

Saturate Minimization

Prior to contacting it with aqueous caustic, the product from the reactor is subjected to saturate minimization conditions using ethylene and a transalkylation catalyst. Transalkylation catalysts useful in the practice of the present invention include Group VIII metal compounds. Nickel and cobalt compounds are preferred. Useful cobalt catalysts include cobalt octanoate and cobalt naphthanate. Useful nickel catalysts include solid nickel, Raney nickel, inorganic nickel salts, organic nickel salts and, preferably, organic-soluble nickel compounds. Useful organic-soluble nickel compounds include nickel carboxylates, such as nickel naphthanate and nickel octanoate. Nickel octanoate, which is commercially available, is especially preferred.

The Group VIII metal-containing catalyst is used in an amount sufficient to transalkylate the tri(higher) alkyl aluminum compounds but not isomerize the normal alpha olefins. Preferably, the Group VIII metal catalyst is used at concentrations of 10–200 parts per billion by weight ("ppb") of Group VIII metal, based on total weight, preferably 20–60 ppb. This is especially true for a nickel-containing transalkylation catalyst. If cobalt is the predominant Group VIII metal in the Group VIII metal-containing catalyst, the catalyst concentration is between about 800 and 50,000 ppb by weight of cobalt, based on total weight. Preferably, the cobalt catalyst concentration is between about 1600 and about 15,000 ppb.[1] A Group VIII metal is the predominant Group VIII metal in the catalyst when that metal is more than about 75% by weight of the Group VIII metals present in the catalyst.

The reaction residence time, transalkylation catalyst concentration and temperature are chosen so that transalkylation occurs, but isomerization of the produced alpha olefins is minimized. Typical residence times are on the order of 5 to 45 minutes, preferably 15 to 20 minutes. Temperatures in the range of about 170° F. to about 200° F., especially about 180° F. to about 190° F. are preferred. The ethylene pressure typically used is about 500 to 600 psig. The transalkylated product is optionally filtered to remove high molecular weight polyethylene.

The transalkylation causes most of the residual tri(higher)alkyl aluminum compounds to be converted to triethylaluminum. Typically, about 85–90% of the residual tri(higher)alkyl aluminum compounds are so converted. When these triethylaluminum compounds are subsequently hydrolyzed with aqueous caustic, they produce ethane, which is easily separated from the alpha olefins. If the tri(higher)alkyl aluminum compounds were not so converted, they would, upon hydrolysis, produce longer chain paraffins which are more difficult to separate from the alpha olefins.

One advantage of the present invention is that no catalyst poison, such as those required by U.S. Pat. No. 4,918,254 to Diefenbach et al., need be used to prevent undesired side reactions, such as isomerization of the alpha olefins to internal olefins.

Metals Removal

The resulting product is treated with aqueous acid or base, e.g., HCl or sodium hydroxide, to deactivate the trialkyl aluminum catalyst and Group VIII metal-containing, e.g., nickel-containing, transalkylation catalyst and convert them to water soluble products. While acid tends to solubilize better, it can attack the metals used in the reaction vessel. Therefore, it is preferred to use aqueous caustic. For example, such treatment can involve the use of aqueous sodium hydroxide having a concentration of about 1 to about 50% by weight, preferably about 5 to about 30% by weight, at a temperature of about 125° F. to about 250° F. and a pressure of about 0 to about 1000 psig, preferably about 10 to about 600 psig. The amount of sodium hydroxide needed is that amount stoichiometrically required to react with the trialkyl aluminum compounds and Group VIII metal, although from about 2 to about 10 times the stoichiometric amount can be used. A preferred ratio of caustic to trialkyl aluminum compounds and Group VIII metal is about 3:1 on a molar basis. Preferred residence times in the caustic hydrolysis step are between 20 and 30 minutes.

In summary, the transalkylated product is subjected to, e.g., caustic hydrolysis using concentrated caustic, such as 25% sodium hydroxide, to produce aluminum and Group VIII metal compounds which will be removed by the aqueous caustic and/or by a subsequent water washing, which removes residual caustic, aluminum and nickel compounds. Phase separation gives a product containing alpha olefin.

It is critical to this process that the residual Group VIII metal in the organic, alpha olefin phase be reduced to extremely low levels, such that no alpha olefin isomerization occurs at a temperature of 570° F. in 15 minutes. This can be accomplished by having a sufficient residence time in the caustic hydrolysis step and ensuring an efficient water-washing and separation step. In a preferred embodiment of the process of this invention, the caustic hydrolysis and water-washing steps are performed in horizontal tanks (as opposed to typical vertical towers) which increase the volume of and contact between the organic and aqueous phases.

Following the caustic hydrolysis, water-washing and phase separation steps, the organic phase (which contains the normal alpha olefins) should be essentially metal-free. As used herein, the term "essentially metal-free" means that essentially all of the aluminum and Group VIII metal has been removed from the organic phase.

If Group VIII metal removal is not sufficient in the hydrolysis and separation steps, residual Group VIII metal will be carried over into the various alpha olefin product distillation towers. Here, at distillation temperatures, residual Group VIII metal can catalyze the undesirable isomerization of the product alpha olefins to internal olefins and thus produce impure product.

Group VIII metal carryover into the $C_{24}$ and higher cuts can also cause problems in the alpha olefin formation reactor. These cuts are used, in part, as diluent for trialkyl aluminum compounds in the alpha olefin formation reactor. The carryover Group VIII metal can cause undesirable olefin isomerization in the alpha olefin formation reactor.

Unfortunately, since the level of Group VIII metal used is so low, its content in the various cuts and products is very difficult to analyze. Concentrations in the range of ppb, when used in metal reactors which can contain other sources of Group VIII metal, have led to an inability to analytically close the loop on the Group VIII metal balance.

However, it can be readily determined whether the Group VIII metal content in a product containing alpha olefins is too high. If the residence times in the caustic hydrolysis and separation steps are sufficiently long, then the level of Group VIII metal in the alpha olefin-containing product will be low enough that when an aliquot of the produced alpha olefin (after water washing) is heated to 570° F. for 15 minutes, the alpha olefin(s) will not isomerize. If the alpha olefins do isomerize, it means that the level of Group VIII metal is too high (i.e., the alpha olefin product is not "metalfree"), and must be lowered by, for example, additional hydrolysis and water washing.

The resulting alpha olefins preferably have less than 0.3 wt % paraffins, more preferably less than 0.2 wt % paraffins, and less than 0.3 wt %, preferably less than 0.2 wt %, cis- and trans-2-olefins.

EXAMPLES

Commercial scale ethylene oligomerization units containing an alpha olefin formation reactor, a caustic wash tower, a water wash tower, a plurality of distillation columns and an alpha olefin bottoms recycle loop were used in the following examples.

Various test runs were made on these commercial units. For certain parameters, it can take as long as one month to achieve steady state conditions after changes are made in the unit's operation, although many parameters respond more quickly. Test runs in commercial units are necessarily of long duration, when the parameters affected take a long time to achieve steady state.

Comparative Example A

Basic Operation Without Saturate Minimization

Triethyl aluminum and ethylene were allowed to react in a commercial tubular alpha olefin formation reactor to produce normal alpha olefin (NAO) product in the manner similar to that described in U.S. Pat. No. 3,482,000. The product was washed with a 25% sodium hydroxide solution in a wash tower in which the approximate volumes of the aqueous and hydrocarbon phases were 110 ft$^3$ and 155 ft$^3$, respectively, representing a caustic-to-hydrocarbon volume ratio of about 0.7:1.0. This was followed by a water wash in a wash tower in which the approximate volumes of the aqueous and hydrocarbon phases were 225 ft$^3$ and 140 ft$^3$, respectively, for a water-to-hydrocarbon volume ratio of 1.6:1.0. Both towers were vertical with internal diameters of 5 feet and 6 feet, respectively. The alpha olefin production rate was 31,000–32,000 lbs/hr. Because of the difference in product densities, this corresponded to a volume of about 785 ft$^3$/hr through the caustic wash tower and a volume of about 750 ft$^3$/hr through the water wash tower. At this production rate, the residence time of the hydrocarbon phase in each wash tower was approximately 11–12 minutes. The washed organic phase was distilled to produce eleven alpha olefin fractions. The C$_{12}$ product fraction was monitored for saturate (dorecane) and internal isomer (2-dodecene) content. Saturate content was typically about 1.3 wt % with internal isomer averaging approximately 0.1 wt %.

The C$_{24-28}$ alpha olefin product fraction was recycled and used as a diluent for the triethyl aluminum catalyst prior to injection into the alpha olefin formation reactors.

Comparative Example B

Comparative Saturate Minimization Test

At the beginning of this test, 200 ppb of nickel (based on an NAO production rate of 31,000–32,000 lbs/hr), as nickel octanoate, was injected continuously into the product stream from the alpha olefin formation reactor just prior to entering the saturate minimization vessel. The product residence time in the saturate minimization vessel was approximately 12 minutes at a temperature of 180°–190° F. and a pressure of 600 psi. Saturate content of the distilled C$_{12}$ product fraction dropped to 0.3%, where it remained during the first three weeks of the test. Internal isomer content increased to 0.3%, somewhat above the level expected based on laboratory observations. In laboratory experiments it had been observed that an internal isomer increase of 0.10–0.15% occurred as a consequence of reducing saturate content. Between days 17 and 21 of the test the internal isomer content increased to an average of 0.5% which is unacceptable.

In response, the concentration of nickel octanoate was gradually decreased. However, the saturate content increased to 0.5% while the internal isomer content decreased to only 0.4%. With further decreases in, followed by a discontinuation of, nickel injection, the saturate and internal isomer content returned slowly to their pre-test levels (as in Example 1). The test was concluded on day 26. This test was deemed a failure, since the objective was to achieve levels of saturate below 0.3%, while maintaining internal olefin levels of 0.3% or less.

This experiment showed that an extremely low level of a suitable nickel catalyst in this system was very effective in lowering the content of saturate or alkane in the alpha olefin product fractions, given a sufficient residence time and appropriate temperature in the saturate minimization vessel. However, the increase in internal isomer content of the alpha olefin product was unacceptable.

Example 1

Saturate Minimization Test at Reduced Production Rates

A 30 day test run was carried out in the commercial alpha olefin unit described in Example 1. At the beginning of the run the alpha olefin production rate was approximately 14,000–14,500 lbs/hr. This resulted in a residence time of about 27 minutes in the saturate minimization vessel and about 24–25 minutes in each of the caustic and water wash towers. The temperature in the saturate minimization vessel was approximately 175° F. with a pressure of about 600 psi. The saturate (dodecane) level in the distilled C$_{12}$ product fraction prior to the beginning of saturate minimization was about 1.3% and the internal isomer level was approximately 0.1%. The production rate remained in the 14,000–15,000 lbs/hr range during the first five days of the test and then it was gradually increased to a maximum of just under 32,000 lbs/hr on day 14. It was maintained at the 31,000–32,000 lbs/hr level until day 18, and then over a period of three days it was decreased to a level of just above 15,000 lbs/hr. Production was held in the 15,000–17,000 lbs/hr range for the remainder of the test.

TABLE 1

| Day | Production rate (lb/hr) | Residence Times (min) Saturate Minimization | Caustic Wash | Water Wash | Temp. (°F.) | Average Nickel Conc. (ppb) | C$_{12}$ Saturate Content (%) | C$_{12}$ Internal Isomer (%) |
|---|---|---|---|---|---|---|---|---|
| 0 | 14,500 | 27 | 25 | 24 | 175° | 0 | 1.30 | 0.10 |
| 1 | 14,500 | 27 | 25 | 24 | 175° | 200 | 0.30–0.40 | " |
| 2 | 15,000 | " | " | " | 180° | 200 | " | " |

TABLE 1-continued

| Day | Production rate (lb/hr) | Residence Times (min) | | | Temp. (°F.) | Average Nickel Conc. (ppb) | $C_{12}$ Saturate Content (%) | $C_{12}$ Internal Isomer (%) |
| --- | --- | --- | --- | --- | --- | --- | --- | --- |
| | | Saturate Minimization | Caustic Wash | Water Wash | | | | |
| 8 | 19,500 | 20 | 19 | 18 | 185° | 165 | 0.25 | " |
| 9 | 22,600 | 17 | 16 | 15 | " | 140 | 0.20 | " |
| 13 | 27,100 | 14 | 13 | 13 | " | 127 | 0.29 | " |
| 14 | 31,700 | 12 | 12 | 11 | " | 148 | 0.34 | 0.14 |
| 15 | 30,800 | 13 | 12 | 11 | " | 169 | 0.30 | " |
| 16 | 30,500 | " | " | " | " | 175 | " | 0.12 |
| 17 | 31,500 | 12 | " | " | " | 175 | 0.27 | 0.12 |
| 18 | 26,300 | 15 | 14 | 13 | " | 175 | " | 0.15 |
| 19 | 23,500 | 17 | 16 | 15 | " | 175 | 0.25 | 0.16 |
| 20 | 15,300 | 26 | 24 | 23 | " | 175 | 0.23 | 0.14 |
| 22 | 15,700 | 25 | 23 | 22 | " | 175 | 0.14 | 0.15 |
| 23–30 | 15,700–17,100 | 25 | 23 | 22 | " | 175 | 0.13–0.17 | 0.15–0.10 |

During days 1 through 5 the nickel level averaged about 200 ppb. Between days 6 and 10 as production increased, the nickel level decreased to about 110 ppb. Over the period of the following week it was slowly increased to a level of approximately 175 ppb where it was maintained for the remainder of the test. The variation of production parameters and the effect on product composition are shown in Table 1 above.

This experiment showed that at low production rates, below 22,000–25,000 lbs/hr in this unit, the saturate minimization process produced alpha olefin product of the desired quality.

Example 2

Saturate Minimization Test Using Horizontal Wash Vessels

A 39 day test was carried out in a commercial alpha olefin unit which differs from that used in Example 1, for the purposes of this discussion, in that the alpha olefin formation reactors have a much greater capacity and in that the saturate minimization vessel and caustic and water wash towers are larger. In addition to being larger, the wash towers are horizontal rather than vertical affording a much larger contact surface between the aqueous and hydrocarbon phases.

The process was carried out in the same manner as that described in Example 1. In the caustic wash tower the approximate volumes of the aqueous and hydrocarbon phases were 590 ft³ and 525 ft³, respectively, representing a caustic-to-hydrocarbon ratio of about 1.1:1.0. The approximate volumes of the aqueous and hydrocarbon phases in the water wash tower were 590 ft³ and 525 ft³, respectively, representing a water-to-hydrocarbon ratio of about 1.1: 1.0. The temperature and pressure in the saturate minimization vessel throughout the test run were 190° F. and 500 psi. The production rate for the duration of the test was in the range of 30,000–32,000 lbs/hr. The residence time in the saturate minimization vessel was approximately 21 minutes and 40 minutes in each of the caustic and water wash towers. The concentration of nickel throughout the test run was approximately 100 ppb. The results are summarized in Table 2.

TABLE 2

| Example | Production rate (lb/hr) | Residence Times (min) | | | Temp. (°F.) | Average Nickel Conc. (ppb) | $C_{12}$ Saturate Content (%) | $C_{12}$ Internal Isomer (%) |
| --- | --- | --- | --- | --- | --- | --- | --- | --- |
| | | Saturate Minimization | Caustic Wash | Water Wash | | | | |
| 2 | 30,000–32,000 | 21 | 40 | 40 | 190° | 100 | 0.15 | 0.20 |
| 3 | 45,000–60,000 | 11–15 | 21–26 | 21–26 | 170° | 60 | 0.24 | 0.23 |

Example 3

Saturate Minimization at Low Nickel Levels

A 44 day test run was performed in the same commercial unit that was described in Example 2. The average nickel level throughout this test run was about 60 ppb. The conditions and results are summarized in Table 2.

The results in Comparative Examples A and B and Example 1 were taken as evidence that the nickel catalyst was not removed completely by the caustic and water wash systems. It was believed that the nickel catalyst had been carried over into the distillation reboilers and towers resulting in undesired isomerization of the alpha olefin product to internal olefin. These, along with the results in Examples 2 and 3 also indicated the requirement for sufficiently sized and efficient caustic and water wash systems to adequately remove the nickel catalyst in order to prevent alpha olefin isomerization.

Example 4

Other Group VIII metal-containing transalkylation catalysts were compared to nickel transalkylation catalysts in bench scale to determine their effectiveness in reducing saturates in the process of this invention.

Bench-Scale Reaction Solution Make-Up

TNOC solution was prepared by adding 10 ml of tri-n-octyl aluminum ("TNOC") to 90 ml of 1-decene under an argon purge. Ni(Oc)₂ catalyst was made by diluting 1.69 ml of nickel(II) octanoate ("Ni(Oc)$_2$") in 1-dodecene from Witco (6.23% Ni, 36.6% Ni(Oc)$_2$) with 1-decene to a concentration of $5.31 \times 10^{-7}$ g Ni(Oc)$_2$/ml.

Iron solution was prepared by diluting 1.33 ml of 52% iron(III) 2-ethylhexanoate in mineral spirits in 100 ml of 1-decene. 1 ml of this solution was diluted to 100 ml with 1-decene, and 1 ml of this solution was diluted to 100 ml with 1-decene to form the iron solution.

Cobalt solution #1 was prepared by refluxing 0.5384 g of solid cobalt(II) cyclohexylbutyrate powder in 70 ml of 1-decene for approximately three hours. On cooling, precipitation occurred, and the solution was dark green. About 30 ml of toluene was added and heated to reflux. Precipitation was again evident, and the mixture was filtered and diluted to 100 ml with 1-decene. The solution was again filtered the following day, and more precipitate was recovered. This solution had a dark green-brown color. About 0.14 g of pink solid was recovered from the filtration steps. 1 ml of this solution was diluted to 100 ml with 1-decene. Cobalt solution #1 was light yellow.

Cobalt solution #2 was prepared by refluxing for 3 hours the 0.14 g of pink solid cobalt obtained from cobalt solution #1 and a small amount of fresh cobalt(II) cyclohexylbutyrate powder in toluene, using an argon purge and water trap. During reflux, the solution was clear and violet. On cooling, a pink precipitate appeared, and the solution was yellow. The mixture was filtered, and about 0.1 g of precipitate was recovered. The solution was diluted to 100 ml with toluene. The cobalt(II) cyclohexylbutyrate concentration was approximately $4 \times 10^{-4}$ g/ml (approximately $1 \times 10^{-6}$ mol/ml).

Example 5

Bench-Scale Saturate RedUction USing Nickel Catalyst

A 100 ml flask under argon purge was charged with 40 ml of 1-decene and 1 ml of undecane. 10 ml of the TNOC solution was added to the flask, and the contents of the flask were heated to 70° C.

10 ml of the Ni(Oc)$_2$ transalkylating catalyst was added to the flask (about $1.53 \times 10^{-8}$ mole nickel), and immediately a 3 ml sample of the contents of the flask was taken. Additional samples were taken at the times indicated in Table 3.

The samples were shaken with 10 ml of 10% NaOH and 10 ml of hexane, then washed with distilled water and passed through 2 ml of Al$_2$O$_3$ in a 5 ml glass pipet.

Samples were analyzed using gas chromatography. The percent transalkylation for Examples 5–11 was calculated by determining the amount of 1-decene that was transalkylated onto TNOC (i.e. subtracting the decane content of the sample taken immediately after adding the transalkylating catalyst from the decane content of the later sample), and then dividing this decane quantity by the maximum amount of 1-decene that could have been transalkylated onto the TNOC catalyst. These calculations are given in Table 3.

Example 6

Bench-Scale Saturate Reduction Using Nickel Catalyst

Example 5 was repeated, substituting 5 ml of Ni(Oc)$_2$ catalyst (about $0.76 \times 10^{-8}$ mole) in place of the 10 ml of Ni(Oc)$_2$ catalyst.

Example 7

Bench-Scale Saturate Reduction Using Nickel and Iron Catalyst

Example 5 was repeated, substituting 5 ml of Ni(Oc)$_2$ catalyst (about $0.76 \times 10^{-8}$ mole) and 5 ml of iron solution (about $0.76 \times 10^{-8}$ mole) in place of the 10 ml of Ni(Oc)$_2$ catalyst. The results of this example show that iron inhibits the saturate reduction process, even when an active saturate reduction catalyst is present.

Example 8

Bench-Scale Saturate Reduction Using Cobalt Catalyst #1

Example 5 was repeated, substituting 5 ml of cobalt solution #1 in place of the 10 ml of Ni(Oc)$_2$ catalyst. Cobalt was not very soluble in 1-decene, and the actual amount of cobalt in solution was difficult to determine due to continued precipitation of cobalt from solution. No more than $5 \times 10^{-7}$ mole of cobalt was in the 5 ml of cobalt catalyst #1 used in this example.

Example 9

Bench-Scale Saturate ReduCtiOn Using Cobalt Catalyst #2

Example 5 was repeated, substituting 2 ml of cobalt solution #2 in place of the 10 ml of Ni(Oc)$_2$ catalyst. Cobalt appeared to be somewhat more soluble and stable in toluene than in 1-decene. No more than $8 \times 10^{-7}$ mole of cobalt was in the 2 ml of cobalt catalyst #2 used in this example.

Example 10

Bench-Scale Saturate Reduction Using Cobalt Catalyst

Example 5 was repeated, substituting 5 ml of a cobalt solution having a concentration of approximately $3.0 \times 10^{-4}$ g cobalt(II) cyclohexylbutyrate per ml and made by the method for making cobalt solution #2 in place of the 10 ml of Ni(Oc)$_2$ catalyst. No more than $3.8 \times 10^{-6}$ mol of cobalt was in the 5 ml of cobalt solution used in this example.

These examples show that a cobalt transalkylating catalyst is also an effective catalyst for use in the process of this invention.

TABLE 3

| Example Number | Type of catalyst | Time Sample Was Taken (minutes after first sample was taken) | Percent Transalkylation |
| --- | --- | --- | --- |
| 5 | nickel | 130 | 65.4 |
| 6 | nickel | 120 | 29.2 |
| 7 | nickel + iron | 120 | 4.2 |
| 8 | cobalt | 120 | 11.0 |
| 9 | cobalt | 120 | 41.5 |
| 10 | cobalt | 120 | 58.0 |

What is claimed is:

1. A process for producing normal alpha olefins having less than 1.0% saturates content, said process comprising:

(a) contacting a trialkyl aluminum compound and ethylene under alpha-olefin formation conditions thereby producing a mixture comprising normal alpha olefins and tri(higher)alkyl aluminum compounds;

(b) contacting at least a portion of said mixture and sufficient ethylene, in the presence of a cobalt-containing transalkylation catalyst, thereby transalkylating substantially all of said tri(higher)alkyl aluminum compounds, said transalkylation catalyst being used in an amount and under conditions which cause transalkylation of said tri(higher)alkyl aluminum compounds, but not isomerization of said normal alpha olefins; and (c) contacting the mixture produced by step (b) with a sufficient amount of aqueous acid or caustic, and water, to produce an organic phase and an aqueous phase, wherein said organic phase has essentially all of said transalkylation catalyst removed.

2. The process of claim 1 wherein the saturates content of said normal alpha-olefins is no more than about 0.6%.

3. The process of claim 1 wherein the saturates content of said normal alpha-olefins is no more than about 0.4%.

4. The process of claim 1 wherein the cobalt-containing transalkylation catalyst comprises cobalt cyclohexylbutyrate.

5. The process of claim 1 wherein the cobalt-containing transalkylation catalyst comprises cobalt naphthanate.

6. The process of claim 1 wherein the cobalt-containing transalkylation catalyst comprises cobalt and nickel.

7. The process of claim 1 wherein the cobalt catalyst is used at concentrations of about 800 to about 50,000 parts per billion by weight of cobalt, based on total weight.

8. The process of claim 7 wherein the cobalt catalyst is used at concentrations of about 1600 to about 15,000 parts per billion by weight of cobalt, based on total weight.

9. The process of claim 1 wherein the trialkyl aluminum compound is triethylaluminum.

10. The process of claim 1 wherein aqueous caustic is used in step (c).

11. In a process for producing normal alpha olefins by contacting a trialkyl aluminum compound and ethylene under alpha olefin formation conditions, thereby producing a mixture comprising normal alpha olefins and tri(higher) alkyl aluminum compounds, and hydrolyzing said mixture, the improvement comprising contacting said mixture of normal alpha olefins and tri(higher)alkyl aluminum compounds, prior to hydrolysis, with ethylene and a cobalt-containing transalkylation catalyst under transalkylation conditions, said transalkylation catalyst being used in an amount and under conditions sufficient to cause transakylation but insufficient to cause isomerization of said normal alpha olefins, wherein said normal alpha olefins contain essentially no transalkylation catalyst after hydrolysis.

12. The process of claim 11 wherein the cobalt-containing transalkylation catalyst comprises cobalt cyclohexylbutyrate.

13. The process of claim 11 wherein the cobalt-containing transalkylation catalyst comprises cobalt naphthanate.

14. The process of claim 11 wherein the cobalt-containing transalkylation catalyst comprises cobalt and nickel.

15. The process of claim 11 wherein the cobalt catalyst is used at concentrations of about 800 to about 50,000 parts per billion by weight of cobalt, based on total weight.

16. The process of claim 15 wherein the cobalt catalyst is used at concentrations of about 1600 to about 15,000 parts per billion by weight of cobalt, based on total weight.

17. The process of claim 11 wherein the transalkylation catalyst is soluble in said normal alpha olefins.

18. In a process for producing normal alpha olefins by contacting a trialkyl aluminum compound and ethylene under alpha olefin formation conditions, thereby producing a mixture comprising normal alpha olefins and tri(higher) alkyl aluminum compounds, and hydrolyzing said mixture, the improvement comprising contacting said mixture of normal alpha olefins and tri(higher)alkyl aluminum compounds, prior to hydrolysis, with ethylene and a cobalt-containing transalkylation catalyst under transalkylation conditions, said transalkylation catalyst being used in an amount and under conditions sufficient to cause transalkylation but insufficient to cause isomerization of said normal alpha olefins, wherein said normal alpha olefins contain essentially no Group VIII metal after hydrolysis.

19. The process of claim 18 wherein the Group VIII metal comprises cobalt or cobalt and nickel.

20. The process of claim 18 wherein the transalkylation catalyst is soluble in said normal alpha olefins.

* * * * *